(12) United States Patent
Sun et al.

(10) Patent No.: US 6,774,280 B2
(45) Date of Patent: Aug. 10, 2004

(54) ALFALFA HYBRIDS HAVING AT LEAST 75% HYBRIDITY

(75) Inventors: Paul Sun, Roscoe, IL (US); Michael Velde, Clinton, WI (US); Danielson B. Gardner, Wilton, CA (US)

(73) Assignee: Dairyland Seed Co., Inc., West Bend, WI (US)

( * ) Notice: Subject to any disclaimer, the term of this patent is extended or adjusted under 35 U.S.C. 154(b) by 0 days.

(21) Appl. No.: 09/773,976

(22) Filed: Jan. 31, 2001

(65) Prior Publication Data

US 2003/0172410 A1 Sep. 11, 2003

(51) Int. Cl.$^7$ .............................. A01H 1/00; A01H 1/02; A01H 1/04; A01H 5/00; A01H 5/10
(52) U.S. Cl. ..................... 800/260; 800/266; 800/267; 800/271; 800/274; 800/298; 435/430; 435/430.1
(58) Field of Search ................................. 800/260, 266, 800/267, 271, 274, 298, 294, 265; 435/430, 430.1

(56) References Cited

U.S. PATENT DOCUMENTS

| | | | |
|---|---|---|---|
| 3,570,181 A | | 3/1971 | Davis |
| 4,045,912 A | * | 9/1977 | Sun .............................. 47/58 |
| 4,644,683 A | | 2/1987 | Jones |
| 5,724,767 A | | 3/1998 | Sun |
| 5,908,974 A | | 6/1999 | McCaslin |
| 5,981,833 A | | 11/1999 | Wise et al. |

OTHER PUBLICATIONS

Childers et al 1972. Evolution of hybrid alfalfa. Agric. Sci. Rev. 10:11–18.*
Poehlman et al. 1986, Chapter 12: Breeding hybrids. pp. 237–289, In: Breeding Field Crops. AVI Publishing, Westport, Conn.*
Viands et al. 1988. Chapter 30, Pollination control: mechanical and sterility. pp 931–960, In: Alfalfa and alfalfa improvement, Agronomy Monograph No. 29. Crop Sci. Soc. of America, Madison, WI.*
Michelmore et al . 1991. Identification of markers linked to disease–resistance genes by bulked segregant analysis: a rapid method to detect markers in specific genomic regions by using segregating populations. PNAS(USA) 8821:9298–9832.*
Hemmat et al.1998. Molecular markers for the scab resistance (Vf) region in apple. J. Amer. Soc. Hort Sci. 123(6):992–996.*

Fehr et al .1987. Chapter 33: Development of synthetic cultivars. pp 417–427, In :Principles of Cultivar Development, vol. 1. Theory and Technique. MacMillan Publishing Company, New York.*
Northrup et al. 1972. Thor alfalfa. Seed Scoop 19(4):6.*
Thompson et al .1974. Registration of Indiana Syn.C alfalfa germplasma. Crop Science 14(4):609.*
Pedersen et al .1973. Alfalfa seed size as an indicator of hybridity. Crop Sci 13:72–75.*
Hill et al. 1981.Effect of the number of parents on performance of alfalfa synthetics. Crop Sci. 21:298–300.*
Rotili et al .1995.Variety constitution methodology in *Medicago sativa*: a model of stand structure, cultivar, and plant. Rasteneiev dni Nauki 32(6):15–17.*
Vos et al. 1995. AFLP: a new technique for DNA fingerprinting. Nucl. Acids Res. 23 210:4407–4414.*
Brummer, E. Charles, Capturing Heterosis in Forage Crop Cultivar Development, *Crop Science*, vol. 39, No. 4, pp. 943–954 (1999).
Putnam, D. et al., "2000 alfalfa cultivar yield and fall dormancy trial results" *Agronomy Progress Report, Agricultural Experimental Station Cooperative Extension UC Davis Department of Agronomy and Range Science*, No. 273, Jan. 2001, 1–24.
Putnam D., et al., "1999 alfalfa cultivar yield and fall dormancy trial results" *Agronomy Progress Report, Agricultural Experimental Station Cooperative Extension UC Davis Department of Agronomy and Range Science*, 1999 No. 267, 2000, 1–7.
Gjuric, R., et al., "Identification of cross–pollinated and self–pollinated progeny in alfalfa through RAPD mulliplex loci analysis" *Crop Science*, vol. 36, No. 2, 1996, 389–393.
Kehr, W.R., "Cross Fertilization in Seed Production in Relation to Forage Yield of Alfalfa" *Crop Science*, vol. 16, No. 1, 1976, 81–86.

* cited by examiner

Primary Examiner—David T. Fox
(74) Attorney, Agent, or Firm—Michael Best & Friedrich LLP

(57) ABSTRACT

Disclosed is a hybrid alfalfa seed deposited as ATCC Accession Number PTA-2759. Also disclosed is a hybrid alfalfa plant or part thereof derived from the seed deposited as ATCC Accession Number PTA-2759. A method of obtaining commercially acceptable production of alfalfa seed having at least 75% hybridity by planting male sterile and male fertile seed at a ratio of about 4:1 is also disclosed.

10 Claims, No Drawings

ALFALFA HYBRIDS HAVING AT LEAST 75% HYBRIDITY

CROSS-REFERENCE TO RELATED APPLICATIONS

Not applicable.

BACKGROUND OF THE INVENTION

Alfalfa (*Medicago sativa*) has often been referred to as the "Queen of Forages" because it is an excellent source of protein and digestible fiber, and because its wide adaptation. Alfalfa is highly effective in nitrogen fixation, and is frequently planted in crop rotation to replenish nutrients depleted from the soil by other crops such as corn.

Efforts to develop alfalfa varieties having improved traits and increased production have focused on breeding for disease, insect, or nematode resistance, persistence, adaptation to specific environments, increased yield, and improved quality. Breeders have had less success in breeding for yield and quality per se, although methods directed toward increasing herbage quality and forage yield have been developed. For example, see U.S. Pat. No. 4,045,912, which is incorporated herein by reference.

Breeding programs typically emphasize maximizing heterogeneity of a given alfalfa variety to improve yield and stability. However, this generally results in wide variations in characteristics such as flowering dates, flowering frequency, development rate, growth rate, fall dormancy and winter hardiness. Prior art breeding methods do not emphasize improving the uniformity of these characteristics.

An important economic consideration in the development of hybrid alfalfa strains is the ability of such hybrids to produce acceptable yields of alfalfa seed. U.S. Pat. No. 4,045,912, incorporated by reference herein, discloses a process for producing alfalfa seed by random pollination of male sterile plants (produced by a cross of a cytoplasmic male sterile line and maintainer alfalfa line) and a male fertile line, with the ratio of male sterile plants to male fertile plants in the range of from 1:1 to 3:1.

There is a need in the art for producing alfalfa hybrids having agronomically desirable traits and breeding methods that result in a high degree of hybridity, uniformity of selected traits, and acceptable seed yields.

BRIEF SUMMARY OF THE INVENTION

In one aspect, the present invention provides a *Medicago sativa* hybrid seed or cultivated alfalfa seed designated DS9705 Hyb ((A833×B209)×(Thor, DS9761 and C580)), and deposited under the terms of the Budapest Treaty on Dec. 4, 2000 with the America Type Culture Collection (ATCC), Manassas, Va., under Accession Number PTA-2759.

The present invention includes a *Medicago sativa* hybrid plant or cultivated alfalfa plant derived from the seed deposited under Accession Number PTA-2759. The plant may be grown directly from the seed deposited under Accession Number PTA-2759, or may be obtained indirectly from a plant grown directly from the seed by any suitable means. For example, the plant may be generated from seed produced by a plant grown directly from the seed, from a cutting taken from a plant grown directly from the seed, or from tissue culture or callous derived from cells from a plant grown directly from the seed. The invention includes succeeding generations of plants derived from plants grown from the seed of Accession Number PTA-2759.

In other aspects, the present invention includes the pollen and ovule of a plant derived from the seed deposited under Accession Number PTA-2759.

In another aspect, the present invention provides a method of producing alfalfa seeds having at least 75% hybridity comprising the steps of: crossing cytoplasmic male sterile alfalfa plants with maintainer alfalfa plants to produce cytoplasmic male sterile hybrid seed; selectively harvesting seed from the cytoplasmic male sterile plants; crossing plants grown from the seed of male sterile hybrid plants by male fertile alfalfa plants by pollination by growing the seed from male sterile hybrid plants with seed from at least one male fertile alfalfa plant, the male sterile and male fertile seed planted at a ratio of about four male sterile seeds to every one male fertile seed; and non-selectively recovering seeds from the pollinated alfalfa plants.

Another aspect of the invention provides seed comprising at least 75% hybrid seed, the seed produced by crossing cytoplasmic male sterile alfalfa plants with maintainer alfalfa plants to produce cytoplasmic male sterile hybrid seed; selectively harvesting seed from the cytoplasmic male sterile plants; crossing plants grown from the seed of male sterile hybrid plants by male fertile alfalfa plants by pollination by growing the seed from male sterile hybrid plants with seed from at least one male fertile alfalfa plant, the male sterile and male fertile seed planted at a ratio of about four male sterile seeds to every one male fertile seed; and non-selectively recovering seeds from the pollinated alfalfa plants.

Optionally, the percentage hybridity can be verified using either genetic or morphological markers.

It is an advantage of the present invention that the method of producing hybrid alfalfa seed results in seed with at least 75% hybridity in commercially acceptable yields.

It is an advantage that any cytoplasmic male sterile alfalfa plants and maintainer alfalfa plants may be selected for use in the practice of the present invention to obtain a cytoplasmic male sterile hybrid plant.

It is a further advantage of the present invention that the forage yields of fields planted with 75% hybrid alfalfa are comparable to forage yields of fields planted with 100% hybrid seed, a feature that allows for high forage yields and high seed production.

Other features and advantages of the invention will be apparent upon review of the specification.

BRIEF DESCRIPTION OF THE SEVERAL VIEWS OF THE DRAWINGS

Not applicable.

DETAILED DESCRIPTION OF THE INVENTION

In one aspect, the present invention includes the hybrid alfalfa seed deposited under the Budapest Treaty on Dec. 4, 2000 with the American Type Culture Collection in Manassas, Va. as Accession Number PTA-2759, and plants or plant parts derived from the seed deposited as Accession Number PTA-2759.

By "a plant derived from the seed deposited as Accession Number PTA-2759", it is meant a plant that is grown directly from the seed deposited as Accession Number PTA-2759, or a plant that is obtained indirectly from a plant grown from the seed deposited as Accession Number PTA-2759. Plants obtained indirectly from a plant grown from the seed deposited as Accession Number PTA-2759 may be grown from a vegetative cutting, seed, callus or tissue culture obtained from a plant or plant part grown from the seed deposited as Accession Number PTA-2759 or a clonal plant thereof.

The present invention also provides a method of obtaining hybrid alfalfa lines using cytoplasmic male sterile alfalfa lines (A lines), maintainer alfalfa lines (B lines), and male fertile pollenizer lines (C lines) as described in detail in the examples.

Male sterile A lines may be identified by evaluating pollen production using the Pollen Production Index (P.P.I.), which recognizes four distinct classes:

1. Male Sterile Plants (MS) PPI=0

No visible pollen can be observed with the naked eye when flower is tripped with a black knife blade.

2. Partial Male Sterile Plant (PMS) PPI=0.1

A trace of pollen is found with the naked eye when flower is tripped with a black knife blade.

3. Partial Fertile Plant (PF) PPI=0.6

Less than a normal amount of pollen can be observed with the naked eye when flower is tripped with a black knife blade.

4. Fertile Plant (F) PPI=1.0

Normal amounts of pollen can be observed when flower is tripped with a black a knife blade.

The cells of the cytoplasmic male sterile (A line) alfalfa plants contain sterile cytoplasm and the non-restorer gene. The maintainer line (B line) is a male and female fertile plant, and when crossed with an A line plant, maintains the male sterility of the cytoplasmic male sterile plant in the progeny. The cells of a maintainer line plant contain normal cytoplasm and the non-restorer gene. Methods for identifying cytoplasmic male sterile and maintainer lines of alfalfa are well known to those versed in the art of alfalfa plant breeding (e.g., see U.S. Pat. No. 3,570,181, which is incorporated by reference herein). A pollenizer line (C line) is a fertile plant containing both male and female parts.

Briefly, the method of the invention is performed as follows:

1. Alfalfa plants with desirable agronomic traits are selected. Male sterile A line plants are selected from male sterile ("female") populations, maintainer B line plants are selected from maintainer populations, and pollenizer C line plants are selected from restorer populations, or from clonal or synthetic populations.

2. The selected A and B lines are grown from cuttings or seed and cross pollinated using bees to produce hybrid male sterile breeder and foundation seeds. Seeds are harvested from cytoplasmic male sterile plants only.

3. Selected pollenizer plants are selfed or interpollinated by bees to produce breeder and foundation pollenizer seeds and the seed is harvested in bulk.

4. For large scale commercial production of hybrids, male sterile seeds and pollenizer seeds are planted at a ratio of male sterile seeds and male fertile (pollenizer) seeds of about 4:1, and the plants grown therefrom are pollinated.

5. Seeds are harvested in bulk from the plants grown from the seed of step 4, above.

6. Optionally, the percentage hybridity can be determined using either genetic or morphological markers.

Cytoplasmic male sterile lines may be maintained by vegetative cuttings. Maintainer lines can be maintained by cuttings or self-pollination. Male sterile hybrids can be obtained by cross-pollinating cytoplasmic male sterile plants with maintainer plants. Pollenizer lines can be maintained by selfing or, if more than two clones are used, by cross-pollination.

Preferably, at least one of the alfalfa plant lines used in developing alfalfa hybrids according to the method of the present invention has at least one desirable agronomic trait, which may include, for example, resistance to disease or insects, cold tolerance, increased persistence, greater forage yield or seed yield, improved forage quality, uniformity of growth rate, and uniformity of time of maturity.

In the controlled pollination step, the cytoplasmic male sterile plants are typically grown in separate rows from the maintainer plants. The plants are pollinated by pollen-carrying insects, such as bees. Segregating the male sterile and maintainer plants facilitates selective harvest of hybrid seed from the cytoplasmic male sterile plants.

The male sterile seed and male fertile seed is preferably provided as a random mixture of the seed in a ratio of about 4:1, which would provide for random distribution of the male sterile and male fertile plants grown therefrom and random pollination of the alfalfa plants. As one of skill in the art will appreciate, one could also practice the method of the invention using designed distribution of male sterile hybrid and male fertile lines within a field and and subsequent pollination by pollen-carrying insects.

In the examples below, male sterile line A833, maintainer line B209, and pollenizer lines Thor, DS9671, and C580 were used. One of ordinary skill in the art will appreciate that any suitable male sterile line, maintainer line, and pollenizer line could be successfully employed in the practice of the method of the invention.

The term "hybrid" as used herein is intended to refer to a cross between a male sterile line and a pollenizer line in which at least about 75% of the seeds differ genetically from the parent lines. The term S1 refers to the first generation of selfing.

Preferably, the method of the invention produces seed having at least about 75% hybridity (i.e., at least 75% of the seeds differ genetically from the male and female parent lines). Estimates of hybridity showed that the method of the invention yielded seeds comprising about 90% hybrids. However, forage yields obtained from fields seeded with 75 or 80% hybrid seed were comparable to forage yields obtained from fields planted with 100% hybrid seeds. Therefore, it is expected that hybrid production seed having 75% hybrid seeds would give forage yields comparable to those obtained from fields planted with 100% hybrid seed.

Preferably, the seed produced by the method of the invention is produced in commercially acceptable yields. Of course, what constitutes a "commercially acceptable seed yield" may vary from line to line, depending on the totality of hybrid's characteristics. Preferably, seed production of plants grown from male sterile hybrid seed crossed with plants grown from male fertile seed planted in a ratio of 4:1 is at least 80% of the average seed production obtained from selfing the male fertile parent. More preferably still, seed production is at least 85% as great as, or even as much as 95% or 100% as great as seed production by the male fertile parent. What constitutes a commercially acceptable seed yield may be made with reference to typical seed production of synthetic alfalfa varieties. In the examples below, hybrid alfalfa seed production yields were comparable to those obtained from synthetic alfalfa varieties such as Magnum V or Magnum IV.

The following non-limiting examples are intended to be purely illustrative.

EXAMPLES

Scoring of Plant Size

Two-month-old seedlings started in the greenhouse were transplanted to the field in April of 1999 with a spacing of 40 inches between plants. Plants were trimmed off in August of 1999 and herbage regrowth visually scored in September of the same year. Plants were scored from 1 to 9, with "1" being the least herbage and "9" greatest herbage. The mean, variance and range of visual scores of plant size are provided in Table 1.

Upon visual inspection, hybrids A833×B209 and A833× B209 (S1) appeared more vigorous than the synthetic varieties Vernal and Saranac and more vigorous than the (S1) progeny of selected clones (Thor, DS9671, C580 and B209). The hybrids also show greater uniformity in size than synthetic varieties, as is evidence by the lower variance.

Survival of Over Wintered Plants

The percentage of plants that survived over the winter of 1999 was determined (Table 2). Hybrids A833×209 and A833×209 (S1) had the highest survival rates at 95.8% and 95.0%, respectively. The synthetic varieties Vernal and Saranac, which had survival rates of 82.2% and 87.9%, respectively.

The survival rate of the progeny of different individual clones varied from 80.4 to 92.7%. Hybrid A833×B209 showed remarkable improvement in winter survival over (S1) progeny of the male parent B209. The formation of hybrids can enhance the ability to survive winter stress.

Assessment of Spring Vigor

Spring vigor of alfalfa plants was assessed and scored from 1–9, with "1" being less vigorous and "9" being most vigorous. The results are summarized in Table 3.

Hybrids, A833×B209 and A833×B209 (S1) showed greater spring vigor and uniformity relative to the synthetic varieties Vernal and Saranac, as well as greater vigor and uniformity than the (S1) progeny of selected clones (Thor, DS9671, C580 and B209).

Flowering Dates

The first and second Julian flowering dates were recorded in June and July-August, respectively, for synthetic varieties Vernal and Saranac, (S1) progeny of selected clones (Thor, DS9761, C580 and maintainer line B209), and hybrids A833×B209 and A833×B209 (S1). The Julian flowering date is measured in days from January $1^{st}$ and is expressed in days. The results are presented in Table 4 and 5.

The hybrids A833×B209 and A833×B209 (S1) had more uniform flowering dates than progeny of the pollinators, maintainer line, or synthetics, as is evidenced by a relatively low variance.

Flower Color

Flower colors were recorded for each alfalfa plant (Table 6).

Pollen Production Index

Four male fertility classifications, male sterile (MS), partial male sterile (PMS), partial fertile (PF), and fertile (F) were used in this research project. The distribution for male sterility of hybrids, A833×B209 and A833×B209 (S1) were recorded and the results are presented in Table 7.

P.P.I. for A833×B209 and A833×B209 (S1) are 0.077 and 0.086 respectively. Slightly increased P.P.I. values were obtained when S1 progeny were used as maintainer line.

Disease Resistance of Hybrid and Hybrid Components

The response of alfalfa plant hybrid DS9705Hyb ((A833× B209)×(Thor, DS9761 and C580)) and hybrid components (B209, A833×B209, Thor, DS9761 and C580) to various diseases was evaluated according to the "Standard Tests to Characterize Alfalfa Cultivars", approved by the North American Alfalfa Improvement Conference. The resistance or susceptibility of the hybrid or hybrid components to anthracnose, bacterial wilt, Fusarium wilt, Verticillium wilt, Phytophthora root rot, Aphanomyces root rot (Race 1), stem nematode and root knot nematode was assessed. For each disease tested, appropriate check cultivars, including resistant and susceptible cultivars, were employed as controls. The results are presented in Tables 8 through 23.

For each type of disease tested, each line of plants was assigned to one of five classes of resistance according to the percentage of resistant plants as follows:

| Class | % Resistant plants |
| --- | --- |
| Susceptible | <6 |
| Low resistant | 6–14 |
| Moderately resistant | 15–30 |

-continued

| Class | % Resistant plants |
| --- | --- |
| Resistant | 31–50 |
| Highly resistant | >50 |

DS9705Hyb was found to be highly resistant to bacterial wilt, Fusarium wilt, Phytophthora root rot, root knot nematode; resistant to anthracnose (race 1), Verticillium wilt, stem nematode and moderately resistant to Aphanomyces root rot (Race 1).

Forage Yields

Forage yields of hybrid DS9705Hyb and the hybrid components B209, A833×B209, Thor, DS9761 and C580 were measured and are presented on Tables 24 and 25. The hybrid DS9705Hyb showed average yields that were 12% higher than those obtained with Vernal over eighty five harvests and twelve test locations.

Persistence Advantage of the Hybrids

Persistence of hybrid DS9705Hyb showed a 15% advantage over check variety Vernal in five test environments. (Table 26)

Seed Yield of Hybrid and Hybrid Components

Alfalfa seed yield is usually greatly affected by cultural management, field conditions and year. Three fields of the alfalfa hybrid DS9705Hyb were planted in the spring of 2000. Hybrid alfalfa seed was obtained at a yield of about 400, 500, and 600 pounds per acre, a yield comparable to that of synthetic varieties. The synthetic variety Magnum V produced seed at a rate of about 400, 500, and 600 pounds per acre; Magnum IV yielded about 375, 450, and 550 pounds seed/per acre in the same year. Seed yield of male sterile foundation seeds A833×B209 was significantly lower than maintainer line B209.

Percentage of Hybrid Required for Maximum Forage Yield

The hybrid A19–616×Thor, showed a forage yield 16% higher than that of the inbred AP-51. To determine the hybrid percentage required for maximum forage yield, fields were seeded with mixtures of hybrid and inbred seeds in different ratios separated by 10% intervals, ranging from 100% hybrid and 0% inbred to 0% hybrid and 100% inbred. The results of the forage yield experiments, which were conducted in Clinton, Wis., Arlington, Wis., and Rosemount, Minn. in 1997 and 1998, are presented in Table 27.

Seed comprising 100% hybrid A19–616×Thor yielded 6.0 tons/per acre, whereas inbred AP-51 yielded 5.19 tons/per acre, with a L.S.D.(0.05) of 0.2. The results show no difference in forage yields of fields planted with from 80–100% hybrid seed, and a slight decrease in forage yields of fields planted with from 50–70% hybrids.

Percent Hybridity of the Hybrid DS 9705Hyb

Seed obtained from non-selective harvest of male sterile hybrids crossed by male fertile plants planted at a ratio of 4:1 includes both hybrid and non-hybrid seed. Molecular markers were identified to allow differentiation of hybrids from parental lines as follows.

Parental plants B209, DS9671, C580 and Thor were selfed and pure S1 seed was generated. Amplified fragment length polymorphism (AFLP) analysis of DNA isolated from plants derived from the parental seed of B209, DS9671, C580, Thor; the hybrid seed of A833×B209; and hybrid seed of DS9705Hyb was conducted by KeyGene Moleculare Marker Services (P.O. Box 216, 6700 AE Wageningen, The Netherlands). The seeds were germinated and grown into plants. DNA was isolated from a pool of 20 individuals from each pedigree. The parental samples were subjected to AFLP using 15 primer combinations, which identified polymorphic markers between the B209, Thor, C580, DS9671 and A833×B209 parents. The two primer pairs, designated E32/M49 and E36/M50, were found to identify the greatest numbers of polymorphisms and were used to amplify DNA in production lots of DS9705Hyb. Primers E32, M49, E36, and M50 have the sequences shown in SEQ ID NO:1, SEQ ID NO:2, SEQ ID NO:3, and SEQ ID NO:4, respectively. Ninety plants were grown from DS 9705Hyb production lot seed and DNA was isolated from each plant individually. The DNA was subjected to AFLP using the two primer pairs. Of the 90 plants tested, 90% were hybrid plants and 10% were male selfs.

TABLE 1

Herbage regrowth scores of alfalfa plants.

| | Herbage regrowth | | | |
|---|---|---|---|---|
| | Number | Mean | Variance | Range |
| Vernal | 136 | 4.35 | 1.07 | 1–7 |
| Saranac | 155 | 4.38 | 0.95 | 2–7 |
| Thor | 129 | 4.37 | 0.69 | 1–7 |
| DS9761 | 115 | 4.43 | 0.51 | 3–6 |
| C580 | 175 | 4.26 | 0.61 | 1–6 |
| B209 | 200 | 4.34 | 0.57 | 2–7 |
| A833x209 | 116 | 4.71 | 0.57 | 2–7 |
| A833x209(S1) | 114 | 4.61 | 0.72 | 1–6 |

Planted: Apr. 23, 1999 at the Dairyland Research Station near Clinton, WI
Scored: 9/99
Rating scale:
1 is least amount of herbage
9 is greatest amount of herbage

TABLE 2

Survival of over wintered alfalfa plants

| | Total plants | Live | Dead | Survival (%) |
|---|---|---|---|---|
| Vernal | 163 | 134 | 29 | 82.2 |
| Saranac | 174 | 153 | 21 | 87.9 |
| Thor | 150 | 131 | 19 | 87.3 |
| DS9671 | 124 | 115 | 9 | 92.7 |
| C580 | 202 | 177 | 25 | 87.6 |
| B209 | 250 | 201 | 49 | 80.4 |
| A833x209 | 120 | 115 | 5 | 95.8 |
| A833x209 (S1) | 120 | 114 | 6 | 95.0 |

Planted: Apr. 23, 1999 at the Dairyland Research Station near Clinton, WI
Scored: 5/00
Rating scale:
By "live" is meant an actively growing plant
By "dead" is meant a non-growing plant

TABLE 3

Spring vigor of alfalfa plants

| | Number | Mean | Variance | Range |
|---|---|---|---|---|
| Vernal | 164 | 5.17 | 6.82 | 1–8 |
| Saranac | 174 | 5.81 | 5.57 | 1–9 |
| Thor | 150 | 5.73 | 5.51 | 1–8 |
| DS9671 | 124 | 5.89 | 3.45 | 1–9 |
| C580 | 202 | 5.59 | 5.98 | 1–9 |
| B209 | 250 | 5.28 | 5.41 | 1–9 |
| A833x209 | 120 | 6.88 | 2.59 | 1–9 |
| A833x209 (S1) | 120 | 6.40 | 2.93 | 1–8 |

Planted: Apr. 23, 1999 at the Dairyland Research Station near Clinton, WI
Scored: 5/00
Rating Scale:
1 is least vigorous;
9 is most vigorous

TABLE 4

First Julian flowering dates (expressed in days from January 1 to first flowering)

| | Number | Mean | Variance | Range |
|---|---|---|---|---|
| Vernal | 133 | 148.6 | 31.1 | 135–159 |
| Saranac | 154 | 148.4 | 28.31 | 134–159 |
| Thor | 129 | 148.5 | 30.57 | 115–159 |
| DS9671 | 115 | 148.4 | 20.38 | 142–159 |
| C580 | 176 | 147.7 | 19.50 | 136–159 |
| B209 | 201 | 147.4 | 18.01 | 135–159 |
| A833x209 | 115 | 145.0 | 11.74 | 137–157 |
| A833x209 (S1) | 114 | 147.2 | 23.70 | 135–159 |

Planted: Apr. 23, 1999 at the Dairyland Research Station near Clinton, WI
Data collected in 2000 growing season

TABLE 5

Second Julian flowering dates (expressed in days from January 1 to second flowering)

| | Number | Mean | Variance | Range |
|---|---|---|---|---|
| Vernal | 133 | 186.5 | 12.87 | 177–195 |
| Saranac | 152 | 185.8 | 11.67 | 175–195 |
| Thor | 132 | 186.2 | 11.41 | 177–195 |
| DS9761 | 115 | 187.1 | 8.19 | 180–195 |
| C580 | 177 | 185.6 | 9.41 | 180–195 |
| B209 | 201 | 184.5 | 13.21 | 176–195 |
| A833x209 | 115 | 185.5 | 4.69 | 177–195 |
| A833x209 (S1) | 114 | 185.9 | 7.58 | 177–195 |

Planted: Apr. 23, 1999 at the Dairyland Research Station near Clinton, WI
Data collected in 2000 growing season

TABLE 6

Flower color classification

| | N | P | BP | B | G | V | W |
|---|---|---|---|---|---|---|---|
| Vernal | 126 | 119 | 0 | 0 | 0 | 3 | 4 |
| Saranac | 149 | 149 | | | | | |
| Thor | 129 | 128 | | | | | 1 |
| DS9761 | 113 | 112 | | | 1 | | |
| C580 | 174 | 172 | 1 | 1 | | | |
| B209 | 194 | 194 | | | | | |
| A833x209 | 114 | 114 | | | | | |
| A833x209 (S1) | 113 | 113 | | | | | |

P = purple;
BP = blue purple;
B = blue,
G = green;
V = variegated;
and W = white.

TABLE 7

Pollen production of readings of A833xB209 and A833 x B209 (S1) in June 2000 at Clinton, Wisconsin

| | Fertility classifications | | | | | |
|---|---|---|---|---|---|---|
| | N | MS | PMS | PF | F | P.P.I |
| A833xB209 | 114 | 91 | 14 | 4 | 5 | .077 |
| A833xB209 (S1) | 106 | 89 | 7 | 4 | 6 | .086 |

| | Rating | PPI Value |
|---|---|---|
| Fertility classifications: | MS | 0.0 |
| | PMS | 0.1 |

TABLE 7-continued

Pollen production of readings of A833xB209 and
A833 x B209 (S1) in June 2000 at Clinton, Wisconsin

| | | |
|---|---|---|
| | PF | 0.6 |
| | F | 1.0 |

TABLE 8

Resistance to anthracnose (Race 1) (*Colletotrichum trifolii*)
Test conducted by Dairyland Research at Clinton, WI

| Variety | Resistance Class | Year Tested | Syn Gen | Unadjusted % R | Adjusted % R |
|---|---|---|---|---|---|
| B209 | R | 1996 | 1 | 29.3 | 30.5 |
| A833xB209 | R | | 1 | 33.3 | 34.7 |
| C580 | R | | 2 | 33.4 | 34.8 |
| DS9671 | HR | | 2 | 54.3 | 56.6 |
| Thor | MR | | 2 | 28.0 | 29.2 |
| Check Varieties | | | | | |
| 1. Saranac AR | R | | | 43.2 | 45.0 |
| 2. Saranac | S | | | 5.0 | 5.2 |
| Test Mean: | | | | 43.8 | 45.6 |
| L.S.D. (.05%) | | | | | 5.2 |
| C.V. (%) | | | | | 8.6 |
| Test Conducted in Lab | | | | | |

Note:
Unadjusted % R is the actual raw data summary.
Adjusted % R is transformed to the standards of the resistant check.

TABLE 9

Resistance to anthracnose (Race 1) (*Colletotrichum trifolii*)
Test conducted by Dairyland Research at Clinton, Wisconsin

| Variety | Resistance Class | Year Tested | Syn Gen | Unadjusted % R | Adjusted % R |
|---|---|---|---|---|---|
| DS9705Hyb | R | 1999 | 1 | 39.2 | 43.9 |
| Check Varieties | | | | | |
| 1. Saranac | ARR | | | 40.2 | 45.0 |
| 2. Saranac | S | | | 3.2 | 3.6 |
| Test Mean: | | | | 32.1 | 42.1 |
| L.S.D. (.05%) | | | | 6.8 | |
| C.V. (%) | | | | 11.6 | |
| Test conducted in Lab | | | | | |

TABLE 10

Resistance to bacterial wilt (*Clavibacter michiganense*)
Test conducted by Dairyland Research at Clinton, WI.

| Variety | Resistance Class | Year Tested | Syn Gen | Unadjusted % R | Adjusted % R | Score A.S.I. |
|---|---|---|---|---|---|---|
| B209 | HR | 1998 | 1 | 63.0 | 73.5 | 1.40 |
| A833xB209 | HR | | 1 | 79.4 | 86.3 | 1.37 |
| C580 | HR | | 2 | 56.2 | 65.6 | 1.96 |
| DS9671 | HR | | 2 | 48.0 | 56.0 | 2.25 |
| Thor | HR | | 2 | 54.0 | 63.0 | 2.28 |
| Check Varieties: | | | | | | |
| 1. Vernal | R | | | 36.0 | 42.0 | 1.80 |
| 2. Narragansett | S | | | 3.0 | 3.5 | 3.8 |
| Test Mean: | | | | 61.0 | 71.1 | 2.4 |
| L.S.D. (.05%) | | | | 13.0 | | .21 |
| C.V. (%) | | | | 30.3 | | 13.8 |
| Test conducted in field. | | | | | | |

Note:
Score A.S.I. is the average severity index. Ratings range from 0–5 with a score of "0" indicating no discernable disease symptoms and "5" indicating plant death.

TABLE 11

Resistance to bacterial wilt (*Clavibacter michiganense*)
Test conducted by Dairyland Research at Clinton, Wisconsin

| Variety | Resistance Class | Year Tested | Syn Gen | Unadjusted % R | Adjusted % R | Score A.S.I. |
|---|---|---|---|---|---|---|
| DS9705Hyb | HR | 1999 | 1 | 63.5 | 74.1 | 1.6 |
| Check Varieties | | | | | | |
| 1. Vernal | R | | | 46.0 | 53.6 | 1.8 |
| 2. Narragansett | S | | | 3.0 | 3.5 | 3.8 |
| Test Mean: | | | | 51.0 | 59.5 | 2.20 |
| L.S.D. (.05%) | | | | 8.2 | | .35 |
| C.V. (%) | | | | 14.2 | | 9.60 |
| Test conducted in field | | | | | | |

TABLE 12

Resistance to Fusarium wilt (*Fusarium oxysporum*)
Test conducted by Dairyland Research at Clinton, WI

| Variety | Resistance Class | Year Tested | Syn Gen | Unadjusted % R | Adjusted % R | Score or A.S.I. |
|---|---|---|---|---|---|---|
| B209 | HR | 1998 | 1 | 70.1 | 75.7 | 1.23 |
| A833xB209 | HR | | 1 | 82.9 | 89.5 | 1.07 |
| C580 | HR | | 2 | 58.2 | 62.9 | 1.71 |
| DS9671 | HR | | 2 | 74.0 | 79.9 | 1.02 |
| Thor | HR | | 2 | 66.0 | 71.3 | 1.66 |
| Check Varieties | | | | | | |
| 1. Agate | R | | | 50.0 | 54.0 | 1.70 |
| 2. MNGN-1 | S | | | 7.9 | 8.6 | 3.45 |
| Test Mean: | | | | 52.0 | 56.2 | 2.6 |
| L.S.D. | | | | 8.2 | | .36 |
| C.V. (%) | | | | 24.1 | | 12.5 |
| Test conducted in field. | | | | | | |

TABLE 13

Resistance to Fusarium wilt (*Fusarium oxysporum*)
Test conducted by Dairyland Research at Clinton, WI

| Variety | Resistance Class | Year Tested | Syn Gen | Unadjusted % R | Adjusted % R | Score or A.S.I. |
|---|---|---|---|---|---|---|
| DS9705Hyb | HR | 1999 | 1 | 72.7 | 78.5 | 1.42 |
| Check Varieties | | | | | | |
| 1. Agate | R | | | 50.0 | 54.0 | 1.56 |
| 2. MNGN-1 | S | | | 0.0 | 0.0 | 3.20 |
| Test Mean: | | | | 62.9 | 67.9 | 1.47 |
| L.S.D. (.05%) | | | | 5.3 | | .26 |
| C.V. (%) | | | | 9.85 | | 6.25 |
| Test conducted in field. | | | | | | |

TABLE 14

Resistance to Verticillium wilt (*Verticillium albo-atrum*)
Test conducted by Dairyland Research at Clinton, Wisconsin

| Variety | Resistance Class | Year Tested | Syn Gen | Unadjusted % R | Adjusted % R |
|---|---|---|---|---|---|
| B209 | R | 1998 | 1 | 37.0 | 32.9 |
| A833xB209 | R | | 1 | 43.0 | 38.2 |
| C580 | R | | 2 | 38.5 | 34.2 |
| DS9671 | R | | 2 | 35.0 | 31.6 |
| Thor | R | | 2 | 41.0 | 36.4 |
| Check Varieties | | | | | |
| 1. Vertus | R | | | 45.0 | 40.0 |
| 2. Saranac | S | | | 4.8 | 4.3 |
| Test Mean: | | | | 38.0 | 33.8 |
| L.S.D. (05%) | | | | 7.8 | |
| C.V. (%) | | | | 13.1 | |

TABLE 14-continued

Resistance to Verticillium wilt (*Verticillium albo-atrum*)
Test conducted by Dairyland Research at Clinton, Wisconsin

| Variety | Resistance Class | Year Tested | Syn Gen | Unadjusted % R | Adjusted % R |
|---|---|---|---|---|---|

Test conducted in Lab

TABLE 15

Resistance to Verticillium wilt (*Verticillium albo-atrum*)
Test conducted by Dairyland Research at Clinton, WI

| Variety | Resistance Class | Year Tested | Syn Gen | Unadjusted % R | Adjusted % R |
|---|---|---|---|---|---|
| DS9705Hyb | R | 1999 | 1 | 36.8 | 33.2 |
| Check Varieties | | | | | |
| 1. Vertus | R | | | 44.3 | 40.0 |
| 2. Saranac | S | | | 5.0 | 4.5 |
| Test Mean: | | | | 22.8 | 20.6 |
| L.S.D. (.05%) | | | | 9.9 | |
| C.V. (%) | | | | 16.2 | |

Test conducted in Lab

TABLE 16

Resistance to Phytophthora root rot (*Phytophthora medicaginis*)
Test conducted by Dairyland Research at Clinton, Wisconsin.

| Variety | Resistance Class | Year Tested | Syn Gen | Unadjusted % R | Adjusted % R |
|---|---|---|---|---|---|
| B209 | MR | 1996 | 1 | 21.8 | 22.8 |
| A833xB209 | R | | 1 | 38.5 | 40.3 |
| C580 | R | | 2 | 42.1 | 44.1 |
| DS9671 | HR | | 2 | 56.5 | 59.2 |
| Thor | HR | | 2 | 66.2 | 69.4 |
| Check Varieties | | | | | |
| 1. Agate | R | | | 31.5 | 33.0 |
| 2. Saranac | S | | | 0.0 | 0.0 |
| Test Mean: | | | | 12.5 | 13.1 |
| L.S.D. (.05%) | | | | 8.6 | |
| C.V. (%) | | | | 14.8 | |

Test conducted in the Lab.

TABLE 17

Resistance to Phytophthora root rot (*Phytophthora medicaginis*)
Test conducted by Dairyland Research at Clinton, Wisconsin.

| Variety | Resistance Class | Year Tested | Syn Gen | Unadjusted % R | Adjusted % R |
|---|---|---|---|---|---|
| DS9705Hyb | HR | 1999 | 1 | 59.2 | 60.0 |
| Check Varieties | | | | | |
| 1. Agate | R | | | 32.6 | 33.0 |
| 2. Saranac | S | | | 0.0 | 0.0 |
| Test Mean: | | | | 48.6 | 49.2 |
| L.S.D. (05%) | | | | 10.6 | |
| C.V. (%) | | | | 16.8 | |

Test conducted in the Lab.

TABLE 18

Resistance to stem nematode (*Ditylenchus dipsaci*)
Test conducted by Dairyland Research at Clinton, Wisconsin.

| Variety | Resistance Class | Year Tested | Syn Gen | Unadjusted % R | Adjusted % R | Score A.S.I. |
|---|---|---|---|---|---|---|
| B209 | R | 1996 | 1 | 39.0 | 42.2 | 3.01 |
| A833xB209 | R | | 1 | 35.0 | 37.8 | 2.55 |
| C580 | R | | 2 | 33.2 | 35.9 | 2.71 |
| DS9671 | R | | 2 | 34.0 | 36.8 | 2.75 |
| Thor | R | | 2 | 29.0 | 31.4 | 3.00 |
| Check Varieites | | | | | | |
| 1. Lahontan | R | | | 37.0 | 40.0 | 3.22 |
| 2. Saranac | S | | | 1.0 | 1.1 | 4.16 |
| Test Mean: | | | | 29.0 | 31.4 | 3.6 |
| L.S.D. (05%) | | | | 7.6 | | .36 |
| C.V. (%) | | | | 11.6 | | 7.6 |

Test conducted in the Lab.

TABLE 19

Resistance to stem nematode (*Ditylenchus dipsaci*)
Test conducted by Dairyland Research at Clinton, Wisconsin.

| Variety | Resistance Class | Year Tested | Syn Gen | Unadjusted % R | Adjusted % R | Score A.S.I. |
|---|---|---|---|---|---|---|
| DS9705Hyb | R | 1999 | 1 | 35.0 | 37.8 | 3.13 |
| Check Varieties | | | | | | |
| 1. Lahontan | R | | | 37.0 | 40.0 | 3.22 |
| 2. Saranac | S | | | 1.0 | 1.1 | 4.16 |
| Test Mean: | | | | 29.0 | 31.4 | 3.6 |
| L.S.D. | | | | | 7.6 | 0.36 |
| C.V. (%) | | | | | 11.6 | 7.6 |

Test conducted in the Lab.

TABLE 20

Resistance to Aphanomyces root rot (Race 1)
(*Aphanomyces euteiches*)
Test conducted by Dairyland Research at Clinton, Wisconsin.

| Variety | Resistance Class | Year Tested | Syn Gen | Unadjusted % R | Adjusted % R |
|---|---|---|---|---|---|
| B209 | LR | 1996 | 1 | 11.2 | 9.5 |
| A833xB209 | MR | | 1 | 20.0 | 17.0 |
| C580 | MR | | 2 | 26.0 | 22.1 |
| DS9671 | MR | | 2 | 19.2 | 16.3 |
| Thor | MR | | 2 | 23.8 | 20.2 |
| Check Varieties | | | | | |
| 1. WAPH-1 | R | | | 58.9 | 50.0 |
| 2. Saranac | S | | | 0.0 | 0.0 |
| Test Mean: | | | | 12.3 | 10.4 |
| L.S.D. (.05%) | | | | | 6.8 |
| C.V. (%) | | | | | 9.9 |

Test conducted in the Lab

TABLE 21

Resistance to Aphanomyces root rot (Race 1)
(*Aphanomyces euteiches*)
Test conducted by Dairyland Research at Clinton, Wisconsin.

| Variety | Resistance Class | Year Tested | Syn Gen | Unadjusted % R | Adjusted % R |
|---|---|---|---|---|---|
| DS9705Hyb | MR | 1999 | 1 | 25.5 | 26.2 |
| Check Varieties | | | | | |
| 1. WAPH-1 | R | | | 48.7 | 50.0 |
| 2. Saranac | S | | | 0.0 | 0.0 |
| Test Mean: | | | | 15.6 | 16.0 |
| L.S.D. (.05%) | | | | | 9.8 |
| C.V. (%) | | | | | 12.6 |

Test conducted in the Lab.

TABLE 22

Resistance to Root-knot nematode (*Meloidogyne halpa*)
Test conducted by Dairyland Research at Clinton, Wisconsin.

| Variety | Resistance Class | Year Tested | Syn Gen | Unadjusted % R | Adjusted % R |
|---|---|---|---|---|---|
| B209 | R | 1996 | 1 | 49.0 | 49.6 |
| A833xB209 | HR | | 1 | 57.0 | 57.6 |
| C580 | R | | 2 | 42.2 | 42.5 |
| DS9671 | HR | | 2 | 59.0 | 59.6 |
| Thor | HR | | 2 | 56.0 | 56.6 |
| Check Varieties | | | | | |
| 1. Nev. SynXX | HR | | | 89.0 | 90.0 |
| 2. Lahontan | S | | | 7.0 | 7.1 |
| Test Mean: | | | | 61.0 | 61.7 |
| L.S.D. (.05%) | | | | | 8.6 |
| C.V. (%) | | | | | 13.6 |

Test conducted in the Lab.

TABLE 23

Resistance to Root-knot nematode (*Meloidogyne halpa*)
Test conducted by Dairyland Research at Clinton, Wisconsin.

| Variety | Resistance Class | Year Tested | Syn Gen | Unadjusted % R | Adjusted % R |
|---|---|---|---|---|---|
| DS9705Hyb | HR | 1999 | 1 | 58.2 | 58.9 |
| Check Varieties | | | | | |
| 1. Nev. Syn XX | HR | | | 89.0 | 90.0 |
| 2. Lahontan | S | | | 7.0 | 7.1 |
| Test Mean: | | | | 58.0 | 58.6 |
| L.S.D. (.05%) | | | | | 9.2 |
| C.V. (%) | | | | | 16.5 |

Test conducted in the Lab.

TABLE 24

Forage Yield of Hybrid DS9705Hyb and Vernal Alfalfa

| FIELD SITE/YEAR | Variety DS9705Hyb Yield (tons/acre) | Vernal Yield (tons/acre) | Harvests |
|---|---|---|---|
| Lansing, MI 1997–99 | 13.63 | 10.88 | 8 |
| Rosemount, MN 1997–99 | 12.49 | 11.48 | 6 |
| Ames, IA 1997–99 | 15.54 | 12.98 | 8 |
| Arlington, WI 1997–99 | 11.08 | 9.48 | 8 |
| Marshfield, WI 1997–99 | 11.33 | 10.01 | 8 |
| Lancaster, WI 1997–99 | 12.09 | 10.53 | 8 |
| Clinton, WI 1997–99 Early | 13.06 | 12.37 | 8 |
| Clinton, WI 1997–99 Medium | 12.64 | 11.72 | 8 |
| Clinton, WI 1997–99 Late | 13.69 | 12.61 | 6 |
| Clinton, WI 1998–99 Early | 9.8 | 8.8 | 6 |
| Clinton, WI 1998–99 Medium | 9.2 | 8.5 | 6 |
| Clinton, WI 1998–99 Late | 10.6 | 9.7 | 5 |
| Total | 145.15 | 130.06 | 85 |
| Percent advantage | 12% | — | |

Note:
Clinton, WI locations are group by maturity at harvest. Early harvests were conducted about 7 days earlier than medium harvests, and late harvests were conducted about 5 days later than medium harvests.

TABLE 25

Forage Yield Data
Data collected across at various Midwest locations
Planting years: 94–98
Harvest years: 94–99

| Component | Percent Vernal | Total Tons | Number of Harvests |
|---|---|---|---|
| A833xB209 | 112.5 | 235.5 | 186 |
| B209 | 101.8 | 126.2 | 86 |
| DS9671 | 110.8 | 141.86 | 124 |
| Thor | 112.9 | 60.62 | 32 |
| C580 | 114.9 | 13.62 | 8 |
| Hybrid | | | |
| DS9705Hyb | 112 | 145.15 | 85 |

TABLE 26

Persistence (% stand) of alfalfa DS9075Hyb and synthetic alfalfa varieties.

| | Early (% stand) | Medium (% stand) | Late (% stand) | Appleton, WI (% stand) | Manawa, WI (% stand) | Mean | Advantage[1] |
|---|---|---|---|---|---|---|---|
| DS9705Hyb | 83 | 82 | 83 | 88 | 87 | 84.6 | 115 |
| Magnum IV | 78 | 79 | 81 | 83 | 82 | 80.6 | |
| Magnum III-Wet | 72 | 77 | 77 | 83 | 82 | 80.6 | |
| DK127 | 73 | 78 | 77 | 77 | 83 | 77.6 | |
| Legendairy 2.0 | 72 | 75 | 77 | 82 | 85 | 78.2 | |
| P5312 | 77 | 80 | 82 | 82 | 82 | 80.6 | |
| P5454 | 77 | 82 | 80 | 83 | 85 | 81.4 | |
| Vernal | 73 | 77 | 77 | 68 | 73 | 73.6 | 100 |

[1]Advantage = (mean % stand for DS9705/mean % stand for Vernal) × 100
Early, medium and late locations are at the Dairyland Research Station at Clinton, WI, planted 5/97 and scored 5/2000.
Appleton, WI, planted 5/97 and scored: 10/2000.
Manawa, WI, planted 5/97 and scored 5/99.

TABLE 27

Forage yield as a function of percent hybrids planted in May, 1996 in Clinton, WI., Arlington, WI., and Rosemount, MN. and harvested in 1997 and 1998.

| Pedigree | |
|---|---|
| Hybrid: | A19-616xThor |
| Male: | AP-51 |

| Ratio Of: | | |
|---|---|---|
| HYBRID | INBRED | YIELD (TONS/ACRE) |
| 100 | 0 | 6.00 |
| 90 | 10 | 6.05 |
| 80 | 20 | 6.04 |
| 70 | 30 | 5.75 |
| 60 | 40 | 5.87 |
| 50 | 50 | 5.81 |
| 40 | 60 | 5.63 |
| 30 | 70 | 5.52 |
| 20 | 80 | 5.41 |
| 10 | 90 | 5.33 |
| 0 | 100 | 5.19 |
| LSD(.05) | | 0.2 |
| CV(%) | | 6.11 |

| | Number of harvests | |
|---|---|---|
| Location: | 1997 | 1998 |
| Arlington, WI | 4 | 4 |
| Rosemount, MN | 3 | 3 |
| Clinton, WI | 4 | 4 |

The present invention is not limited to the exemplified embodiments, but is intended to encompass all such modifications and variations as come within the scope of the following claims.

It is claimed:

1. A Medicago sativa or cultivated alfalfa seed deposited as ATCC Accession Number PTA-2759.

2. A *Medicago sativa* hybrid or cultivated alfalfa plant that is grown directly from the seed deposited as ATCC Accession Number PTA-2759, or a plant grown from a vegetative cutting, obtained from a plant part grown from the seed deposited as ATCC Accession Number PTA-2759, or a clonal plant thereof.

3. Pollen from the plant of claim 2.

4. An ovule from the plant of claim 2.

5. A method of producing alfalfa seeds having at least 75% hybridity comprising the steps of:
   (a) crossing by controlled pollination cytoplasmic male sterile alfalfa plants with maintainer line alfalfa plants to produce cytoplasmic male sterile hybrid plants;
   (b) selectively harvesting seed from the cytoplasmic male sterile hybrid plants of step (a);
   (c) crossing male sterile hybrid alfalfa plants by male fertile alfalfa plants by allowing open pollination of plants grown from the seed of step (b) and seed from at least one line of male fertile alfalfa plants, the male sterile seed and male fertile seed planted at a ratio of about 4:1; and
   (d) non-selectively recovering the seeds from the pollinated alfalfa plants of step (c).

6. The method of claim 5, further comprising the step of determining the hybridity of the progeny of the crossing.

7. The method of claim 6, wherein the step of determining the hybridity of the progeny of the crossing is with a genetic or morphological marker.

8. The method of claim 6, wherein the step of determining the hybridity is accomplished with amplified fragment length polymorphism analysis.

9. The method of claim 5, wherein the average seed yield of step (d) is at least 80% of the average seed yield obtainable by selfing the male fertile plants of step (c).

10. A *Medicago sativa* hybrid or cultivated alfalfa plant regenerated from a callus or tissue culture obtained from a plant part grown from the seed deposited as ATCC Accession No. PTA-2759, wherein said regenerated plant has all of the morphological and physiological characteristics of a hydrib alfalfa plant grown from seed deposited as ATCC Accession No. PTA-2759.

* * * * *

SEQUENCE LISTING

<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: dna
      primer

<400> SEQUENCE: 1
gactgcgtac caattcaac                                                19

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: dna
      primer

<400> SEQUENCE: 2
gatgagtcct gagtaacag                                                19

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: dna
      primer

<400> SEQUENCE: 3
gactgcgtac caattcacc                                                19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: dna
      primer

<400> SEQUENCE: 4
gatgagtcct gagtaacat                                                19